US011992578B2

(12) United States Patent
Muto et al.

(10) Patent No.: US 11,992,578 B2
(45) Date of Patent: May 28, 2024

(54) METHOD FOR PRODUCING ZIRCONIA MATERIAL

(71) Applicants: Orbray Co., Ltd., Tokyo (JP); Tokyo Metropolitan Public University Corporation, Tokyo (JP)

(72) Inventors: Hikaru Muto, Tokyo (JP); Satoshi Kobayashi, Tokyo (JP)

(73) Assignees: Orbray Co., Ltd., Tokyo (JP); Tokyo Metropolitan Public University Corporation, Tokyo (JP)

(*) Notice: Subject to any disclaimer, the term of this patent is extended or adjusted under 35 U.S.C. 154(b) by 154 days.

(21) Appl. No.: 17/319,145

(22) Filed: May 13, 2021

(65) Prior Publication Data
US 2021/0308324 A1 Oct. 7, 2021

Related U.S. Application Data

(63) Continuation of application No. PCT/JP2019/044718, filed on Nov. 14, 2019.

(30) Foreign Application Priority Data

Nov. 16, 2018 (JP) ................. 2018-215669

(51) Int. Cl.
| | | |
|---|---|---|
| A61L 27/32 | (2006.01) | |
| A61L 27/10 | (2006.01) | |
| C04B 35/488 | (2006.01) | |
| C04B 41/85 | (2006.01) | |

(52) U.S. Cl.
CPC .............. *A61L 27/32* (2013.01); *A61L 27/10* (2013.01); *C04B 35/488* (2013.01); *C04B 41/85* (2013.01); *A61L 2430/02* (2013.01)

(58) Field of Classification Search
CPC ....... A61L 27/32; A61L 27/00; C04B 35/447; A61C 8/00
See application file for complete search history.

(56) References Cited

U.S. PATENT DOCUMENTS 4,626,392 A * 12/1986 Kondo .................. C04B 35/447
501/153
2008/0274160 A1 11/2008 Kashiwabara et al.

FOREIGN PATENT DOCUMENTS

| | | |
|---|---|---|
| CN | 102397584 A | 4/2012 |
| CN | 104591782 A | 5/2015 |
| CN | 107056283 A | 8/2017 |
| CN | 107857577 A | 3/2018 |
| CN | 108035143 A | 5/2018 |
| JP | 60-203263 A | 10/1985 |

(Continued)

OTHER PUBLICATIONS

International Search Report (ISR) dated Jan. 21, 2020 filed in PCT/JP2019/044718.

(Continued)

*Primary Examiner* — Dah-Wei D. Yuan
*Assistant Examiner* — Andrew J Bowman
(74) *Attorney, Agent, or Firm* — RANKIN, HILL & CLARK LLP

(57) ABSTRACT

A zirconia material manufacturing method includes: dispersing hydroxyapatite powder in water to prepare a slurry having a hydroxyapatite powder concentration of 1%; and dipping zirconia in the slurry to form, on the zirconia, a coating layer containing hydroxyapatite.

2 Claims, 1 Drawing Sheet

(56) References Cited

FOREIGN PATENT DOCUMENTS

| | | | | |
|---|---|---|---|---|
| JP | 62-297284 A | 12/1987 | | |
| JP | S62297284 | * 12/1987 | .............. | A61C 8/00 |
| JP | 63-201076 A | 8/1988 | | |
| JP | 11-128335 A | 5/1999 | | |
| JP | H11128335 | * 5/1999 | ............. | A61L 27/00 |
| JP | 2008284349 A | 11/2008 | | |
| JP | 2017127798 A | 7/2017 | | |

OTHER PUBLICATIONS

Chinese Office Action (CNOA) issued on Feb. 28, 2023 for the corresponding Chinese Patent Application No. 201980074857.9.

* cited by examiner

METHOD FOR PRODUCING ZIRCONIA MATERIAL

CROSS-REFERENCE TO RELATED APPLICATION

The present application is a continuation application of International Application No. PCT/JP2019/044718, filed on Nov. 14, 2019, which claims priority to Japanese Patent Application No. 2018-215669, filed on Nov. 16, 2018. The contents of these applications are incorporated herein by reference in their entirety.

BACKGROUND ART

1. Technical Field

One aspect of the present disclosure relates to a zirconia material manufacturing method.

2. Related Art

A so-called implant material such as an artificial bone is a biocompatible material which can be used in a manner substantially similar to that of a bone, and is bonded to a remaining bone in a case where a natural bone is missing. Specifically, hydroxyapatite is useful for treatment of a missing portion of a bone.

Ceramics such as zirconia (zirconium dioxide: $ZrO_2$) have properties such as chemical durability, strength properties, thermal resistance, harmlessness in terms of a health aspect, and biocompatibility, and therefore, are used as a biological reinforcement material for an artificial bone or the like.

However, the mechanical strength of the hydroxyapatite is low such as about ¼ to ¹/₁₀ of that of the zirconia, and workability of the hydroxyapatite into a precise shape is low. For these reasons, applications of the hydroxyapatite are limited.

For overcoming these disadvantages, study has been conducted on generation of hydroxyapatite as a coating layer on a surface of zirconia as a base material (see, e.g., JP-A-62-297284).

An object of the technique of JP-A-62-297284 is to provide, for repairing a missing portion of a bone, a ceramics composite having both of favorable mechanical properties (a mechanical strength and workability) as shown in zirconia and biocompatibility as shown in hydroxyapatite. Specifically, this technique is characterized in that a coating layer on ceramics is sintered such that a bonding strength between the ceramics and the coating layer increases.

Moreover, JP-A-62-297284 also discloses a manufacturing method in which the coating layer is formed on zirconia by, e.g., a slurry application method or a slurry pressure impregnation method. The granularity of a raw material in the slurry application method and the slurry pressure impregnation method is a particle size of equal to or less than 1 μm. Fine powder that powder with a particle size of equal to or less than 1 μm covers 100% of the fine powder is added to water or an organic solvent to prepare a slurry with a solid content ratio of 50% to 70%. Using such a slurry, the coating layer is formed. Thereafter, the coating layer is dried at a temperature within a range of 100° C. to 500° C., and in this manner, the coating layer only with the fine powder is formed.

Further, after formation of the coating layer, the coating layer and the zirconia are sintered, and in this manner, the molten coating layer and the molten zirconia are mixed to form a mixed intermediate layer. Thus, a sintered body exhibiting favorable adhesion between the coating layer and the zirconia is generated.

SUMMARY

A zirconia material manufacturing method includes: dispersing hydroxyapatite powder in water to prepare a slurry having a hydroxyapatite powder concentration of 1%; and dipping zirconia in the slurry to form, on the zirconia, a coating layer containing hydroxyapatite.

DETAILED DESCRIPTION

Figure 1:
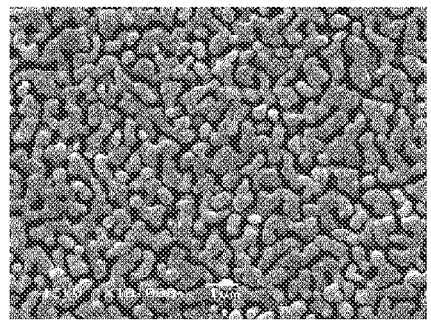
FIG. 1 is a SEM photograph of a coating layer surface of a zirconia material manufactured by a zirconia material manufacturing method according to an example of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

As described above, for applying the zirconia and the hydroxyapatite to the biological reinforcement material, the biocompatibility with a natural bone and the mechanical strength of a joint portion need to be ensured. However, as a result of verification of the ceramics composite of JP-A-62-297284 by the applicant of the present application, the following has been found. That is, in a case where the solid content ratio of the fine hydroxyapatite powder in the slurry is 50% to 70%, the coating layer made of the slurry is separated from the base material. Thus, this ceramics composite is less likely to function as the biological reinforcement material.

One object of the present disclosure is to achieve a zirconia material manufacturing method for providing a zirconia material capable of reducing separation between a coating layer made of hydroxyapatite and zirconia and functioning as a biological reinforcement material.

A zirconia material manufacturing method according to an aspect of the present disclosure (the present manufacturing method) includes: dispersing hydroxyapatite powder in water to prepare a slurry having a hydroxyapatite powder concentration of 1%; and dipping zirconia in the slurry to form, on the zirconia, a coating layer containing hydroxyapatite.

In one embodiment of the present manufacturing method, the dipping the zirconia preferably includes heating the zirconia to 1050° C. and dipping the heated zirconia in the slurry.

Moreover, in one embodiment of the present manufacturing method, the forming the coating layer may include the thickness of the coating layer being 0.5 jum.

According to the present manufacturing method, the zirconia material capable of reducing separation between the coating layer containing the hydroxyapatite and the zirconia and functioning as the biological reinforcement material can be provided.

A zirconia material manufacturing method according to a first feature of the present embodiment includes dispersing hydroxyapatite powder in water to prepare a slurry having a hydroxyapatite powder concentration of 1% and dipping zirconia in the slurry to form, on the zirconia, a coating layer containing hydroxyapatite.

In a zirconia material manufacturing method according to a second feature, the dipping the zirconia in the zirconia material manufacturing method according to the first feature includes heating the zirconia to 1050° C. and dipping the heated zirconia in the slurry.

According to these manufacturing methods, the zirconia material capable of reducing separation between the coating layer made of the hydroxyapatite and the zirconia and functioning as the biological reinforcement material can be provided.

Note that in the present embodiment, the water includes deionized water.

Moreover, the zirconia (zirconium dioxide: $ZrO_2$) includes a sintered dense body substantially with no holes and a sintered porous body having multiple holes with a hole diameter of equal to or greater than 10 µm.

Further, the concentration of the hydroxyapatite powder of the slurry is a volume percent concentration.

When the concentration of the hydroxyapatite powder of the slurry is set to below 1%, it takes full seven days or longer as the time for dipping the coating layer in simulated body fluid (SBF) to generate bone-like apatite from the coating layer. Thus, the applicant of the present application has found by verification that mass productivity of the zirconia material having bioactivity is degraded in this case.

On the other hand, when the concentration of the hydroxyapatite powder of the slurry is set beyond 1%, separation between the coating layer containing the hydroxyapatite and the zirconia is caused. Thus, the zirconia material lacks a mechanical strength between the coating layer and the zirconia, and for this reason, the zirconia material functioning as the biological reinforcement material cannot be provided.

Further, in this case, it takes 24 hours or longer as the time for dipping the coating layer in the SBF until the bone-like apatite is generated from the coating layer. Thus, in this case, the applicant of the present application has also found by verification that the mass productivity of the zirconia material having the bioactivity is degraded.

In a zirconia material manufacturing method according to a third feature, the forming the coating layer in the zirconia material manufacturing method according to the first or second feature includes the thickness of the coating layer being 0.5 µm.

According to this manufacturing method, the bone-like apatite can be, in addition to the above-described advantageous effects, formed from the coating layer containing the hydroxyapatite.

Note that in the present embodiment, the thickness of the coating layer indicates an average thickness across the entire surface of the coating layer in a coating layer surface direction.

The applicant of the present application has found the following by verification. That is, in a case where the thickness of the coating layer is set to less than 0.5 µm or greater than 0.5 µm, the time for dipping the coating layer in the SBF until the bone-like apatite is generated from the coating layer is a day or longer (24 hours or longer). Thus, the applicant of the present application has also found by verification that the mass productivity of the zirconia material having the bioactivity is degraded in this case.

Hereinafter, an example according to the present disclosure will be described. Note that the technique of the present disclosure is not limited only to the following example.

Example

The method for manufacturing a zirconia material according to the present example will be described below. First, zirconia (zirconium dioxide: $ZrO_2$) as a base material and a slurry were prepared. Zirconia as a sintered dense body with no holes or zirconia as a porous body having multiple holes with a hole diameter of equal to or greater than 10 µm was used as the zirconia. Considering application of the zirconia to a biological reinforcement material, the zirconia is more preferably zirconia containing yttria (yttrium oxide: $Y_2O_3$) in terms of ensuring of a higher mechanical strength (specifically a bending strength). Specifically, examples of such zirconia include 2Y zirconia (zirconia containing 2 mol % of yttria), 2.5Y zirconia (zirconia containing 2.5 mol % of yttria), 3Y zirconia (zirconia containing 3 mol % of yttria), and 8Y zirconia (zirconia containing 8 mol % of yttria). In the present example, polycrystalline zirconia as a dense body containing no yttria and having a density of 99% was prepared. The polycrystalline zirconia is obtained by sintering for two hours at a temperature within a range of 1350° C. to 1450° C.

On the other hand, a substance obtained in such a manner that hydroxyapatite powder is dispersed in water was prepared as the slurry. Deionized water was used as the water. The hydroxyapatite ($Ca_{10}(PO_4)_6(OH)_2$) as a powder raw material was obtained in such a manner that commercially-available sintered hydroxyapatite is, by a ball mill, crushed to pieces having an average particle size of 0.1 µm. Of such hydroxyapatite powder with an average particle size of 0.1 µm, 100 parts by weight were dispersed in the water. Upon dispersion, the concentration of the hydroxyapatite powder of the slurry was set to 1% in terms of a volume percent concentration. For example, a dispersant, a binder, and/or a thickener may be added to the slurry as necessary. Note that these additives were not used in the present example.

The zirconia was dipped in the slurry with the slurry contacting part of a zirconia surface. As a dipping method, injection of the zirconia into the slurry or application of the slurry onto part of the zirconia surface may be used. In the present example, the zirconia was heated to 1050° C. in advance of dipping in the slurry. The applicant of the present application has found by verification that wettability of the zirconia with the slurry, adhesion of the slurry to the zirconia, and applicability of the slurry to the zirconia are improved by heating of the zirconia to 1050° C. before dipping in the slurry.

The heated zirconia was cooled. Thereafter, part of the zirconia surface was dipped in the slurry. The zirconia surface to be dipped in the slurry was a polished surface. A dipping time was set to five minutes.

After dipping, the water was removed from the slurry, and accordingly, the slurry was dried. In this manner, a coating layer containing the hydroxyapatite and covering the zirconia was formed on the zirconia. As described above, a zirconia material containing the zirconia and the coating layer was produced.

A SEM photograph (a magnification is 10,000×) of a surface of the formed coating layer is shown in FIG. 1. It has been confirmed that hydroxyapatite powder particles are bound to each other in the formed coating layer as shown in FIG. 1 and the coating layer is in the form of a porous structure in which pores among the bound particles communicate with each other. Moreover, the thickness of the formed coating layer was set to 0.5 μm. Note that the thickness of the coating layer indicates an average thickness across the entire surface of the coating layer in a coating layer surface direction.

After formation of the coating layer, thermal treatment was performed for the coating layer for two hours at a temperature within a range of 1050° C. to 1250° C. Further, after such thermal treatment, the coating layer was dipped in simulated body fluid (SBF) adjusted to a pH of 7.4 and a temperature of 36.5° C. Then, a dipping time until bone-like apatite is generated was measured. The used SBF had an inorganic ion concentration ([mM]: $Na^+$ 142.0, $K^+$ 5.0, $Mg^{2+}$ 1.5, $Ca^{2+}$ 2.5, $Cl^-$ 148.8, $HCO^{3-}$ 4.2, $HPO_4^{2-}$ 1.0, $SO_4^{2-}$ 0.5) substantially equal to that of the human blood plasma.

Figure 2:
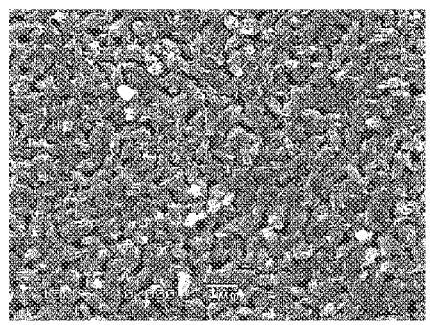
FIG. 2 is a SEM photograph of the coating layer surface of the zirconia material shown in FIG. 1, the coating layer surface being observed after having been dipped in SBF for 12 hours.

As a result, it has been found that the dipping time until the bone-like apatite is generated from the coating layer is at least 12 hours. It has been confirmed that after dipping for 12 hours, the bone-like apatite is generated on the surface of the coating layer as shown in FIG. 2 (a magnification is 10,000×).

According to the method for manufacturing the zirconia material according to the present example, it has been confirmed that the zirconia material capable of reducing separation between the coating layer containing the hydroxyapatite and the zirconia can be achieved as shown in FIG. 1. Thus, the zirconia material functioning as the biological reinforcement material can be provided.

Further, according to the method for manufacturing the zirconia material according to the present example, the following advantageous effect is obtained in addition to the above-described advantageous effect. That is, the bone-like apatite can be formed from the coating layer containing the hydroxyapatite as clearly shown in FIG. 2.

It has been confirmed that due to the thermal treatment after dipping of the zirconia in the slurry, a modified layer (calcium zirconium oxide) that calcium enters the zirconia surface is formed between the coating layer and the zirconia. With formation of such a modified layer, adhesion between the coating layer and the zirconia is improved.

The applicant of the present application has found by verification that in a case where the temperature of heating of the zirconia after dipping in the slurry is lower than 1050° C., almost no reaction is made between the zirconia and the hydroxyapatite and the force of bonding the coating film containing the hydroxyapatite to the zirconia is less likely to increase.

Moreover, the applicant of the present application has found by verification that the bone-like apatite is less likely to be generated from the coating layer in a case where the temperature of heating of the zirconia exceeds 1250° C.

Next, the method for manufacturing a zirconia material according to a first comparative example will be described below. The same zirconia as that of the above-described example was prepared as a base material. On the other hand, as a slurry of the first comparative example, a slurry similar to that used in the example was used, except that the concentration of hydroxyapatite powder of the slurry was changed to 10% which exceeds 1%. The zirconia was dipped in the slurry with the slurry contacting part of a zirconia surface. The same dipping conditions as those of the above-described example were applied. Note that in the first comparative example, the zirconia was also heated to 1050° C. in advance of dipping of the slurry.

Figure 3:
FIG. 3 is a SEM photograph of a coating layer surface of a zirconia material obtained by a comparison example.

An attempt was made to remove water from the slurry after dipping and dry the slurry, thereby forming a coating layer containing the hydroxyapatite and covering the zirconia. In this manner, the zirconia material containing the zirconia and the coating layer was produced. A SEM photograph (a magnification is 50×) of a coating layer surface obtained as a result of such production is shown in FIG. 3. As shown in FIG. 3, separation of the coating layer from the zirconia surface was observed in the first comparative example.

As a result of observation as shown in FIG. 3, it has been found that when the concentration of the hydroxyapatite powder of the slurry is set beyond 1%, separation between the coating layer containing the hydroxyapatite and the zirconia is caused. That is, the following is derived from the observation result. That is, the zirconia material of the first comparative example lacks a mechanical strength between the coating layer and the zirconia due to separation. For this reason, it is difficult for the manufacturing method of the first comparative example to provide the zirconia material functioning as a biological reinforcement material.

The thickness of an unseparated portion of the coating layer shown in FIG. 3 was measured. As a result, a value within a range of 6.0 μm to 8.0 μm was obtained. Thermal treatment was performed for such an unseparated portion of the coating layer for two hours at 1050° C. Further, the coating layer was dipped in SBF adjusted to a pH of 7.4 and a temperature of 36.5° C. after the thermal treatment. Then, a dipping time until bone-like apatite is generated was measured.

As a result, it has been found that the dipping time until the bone-like apatite is generated from the coating layer is at least 24 hours. Thus, the following has been found. That is, in a case where the concentration of the hydroxyapatite powder of the slurry is set beyond 1%, the time for dipping the coating layer in the SBF until the bone-like apatite is generated from the coating layer is 24 hours or longer. Thus, in this case, mass productivity of the zirconia material having bioactivity is degraded as compared to that of the above-described example.

Next, the method for manufacturing a zirconia material according to a second comparative example will be described below. The same zirconia as that of the above-described example was prepared as a base material. On the other hand, as a slurry of the second comparative example, a slurry similar to that used in the example was used, except that the concentration of hydroxyapatite powder of the slurry was changed to 0.30% which is below 1%. The zirconia was dipped in the slurry with the slurry contacting part of a zirconia surface. The same dipping conditions as those of the above-described example were applied. Note that in the second comparative example, the zirconia was also heated to 1050° C. in advance of dipping of the slurry.

Water was removed from the slurry after dipping, and accordingly, the slurry was dried. In this manner, a coating layer containing the hydroxyapatite and covering the zirconia was formed. In this manner, a zirconia material containing the zirconia and the coating layer was produced. The thickness of the formed coating layer was within a range of 0.1 μm to 0.3 μm.

Thermal treatment was performed for the coating layer for two hours at 1050° C. Further, the coating layer was dipped in SBF adjusted to a pH of 7.4 and a temperature of 36.5°

C. after the thermal treatment. Then, a dipping time until bone-like apatite is generated was measured.

As a result, it has been found that the dipping time until the bone-like apatite is generated from the coating layer is at least full seven days (168 hours). Thus, the following has been found. That is, in a case where the concentration of the hydroxyapatite powder of the slurry is set to below 1%, the time for dipping the coating layer in the SBF until the bone-like apatite is generated from the coating layer is full seven days or longer. Thus, in this case, mass productivity of the zirconia material having bioactivity is degraded as compared to that of the above-described example.

According to the example, the first comparative example, and the second comparative example as described above, the following has been found. That is, in the first and second comparative examples where the thickness of the coating layer was set to less than 0.5 µm or greater than 0.5 µm, the time for dipping the coating layer in the SBF until the bone-like apatite is generated from the coating layer is a day or longer (24 hours or longer). Thus, it has been found that as compared to the example where the thickness of the coating layer is set to 0.5 µm, the mass productivity of the zirconia material having the bioactivity is degraded in the first comparative example and the second comparative example.

On the other hand, it has been also found that even when the thickness of the coating layer is set to 0.5 µm, if the time for dipping the coating layer in the SBF is shorter than 12 hours, the bone-like apatite is less likely to be generated from the coating layer and it is difficult to obtain the zirconia material functioning as the biological reinforcement material.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

The invention claimed is:

1. A zirconia material manufacturing method comprising:
   dispersing hydroxyapatite powder in water to prepare a slurry having a hydroxyapatite powder concentration of 1%;
   dipping zirconia in the slurry to form, on the zirconia, a coating layer containing hydroxyapatite; and
   after forming the coating layer, performing a thermal treatment for the coating layer at a temperature within a range of 1050° C. to 1250° C., wherein
   the forming the coating layer includes a thickness of the coating layer being 0.5 µm, and
   a surface of the zirconia to be dipped in the slurry is a polished surface.

2. The zirconia material manufacturing method according to claim 1, wherein
   the dipping the zirconia includes heating the zirconia to 1050° C. and dipping the heated zirconia in the slurry.

* * * * *